(12) United States Patent
Okazaki

(10) Patent No.: US 11,170,522 B2
(45) Date of Patent: Nov. 9, 2021

(54) STORAGE MEDIUM STORING IMAGE PROCESSING PROGRAM, AND IMAGE PROCESSOR

(71) Applicant: KONICA MINOLTA, INC., Tokyo (JP)

(72) Inventor: Tomoya Okazaki, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/669,846

(22) Filed: Oct. 31, 2019

(65) Prior Publication Data

US 2020/0167947 A1 May 28, 2020

(30) Foreign Application Priority Data

Nov. 22, 2018 (JP) .............................. JP2018-219075

(51) Int. Cl.
*G06T 7/70* (2017.01)
*G06K 9/00* (2006.01)
*G06T 7/20* (2017.01)

(52) U.S. Cl.
CPC ............ *G06T 7/70* (2017.01); *G06K 9/00335* (2013.01); *G06T 7/20* (2013.01); *G06T 2207/20084* (2013.01); *G06T 2207/30196* (2013.01)

(58) Field of Classification Search
CPC .......... G06T 7/70; G06T 7/20; G06K 9/00335
See application file for complete search history.

(56) References Cited

U.S. PATENT DOCUMENTS

| 2013/0100284 A1* | 4/2013 | Fujii | A61B 5/1117 |
| | | | 348/135 |
| 2014/0184889 A1* | 7/2014 | Wada | H04N 5/232122 |
| | | | 348/353 |
| 2014/0363089 A1* | 12/2014 | Uetsuji | G06T 7/50 |
| | | | 382/199 |
| 2015/0109442 A1* | 4/2015 | Derenne | G16H 40/67 |
| | | | 348/143 |
| 2015/0324637 A1* | 11/2015 | Utsunomiya | G16H 20/70 |
| | | | 382/107 |
| 2017/0255947 A1* | 9/2017 | Horikawa | G06Q 30/0201 |
| 2018/0174320 A1* | 6/2018 | Hayashi | G06K 9/00342 |

(Continued)

FOREIGN PATENT DOCUMENTS

| JP | 6119938 B2 | 4/2017 |
| JP | 2017-127593 A | 7/2017 |
| JP | 2018-057596 A | 4/2018 |

OTHER PUBLICATIONS

Extended European Search Report issued in corresponding European Application No. 19204847.8, dated Mar. 11, 2020 (9 pages).

(Continued)

*Primary Examiner* — Md K Talukder
(74) *Attorney, Agent, or Firm* — Osha Bergman Watanabe & Burton LLP

(57) ABSTRACT

A non-transitory recording medium storing a computer readable image processing program that causes a computer to: obtain a captured image; detect, from the obtained image, a person area representing a person and an object area representing a predetermined object; detect positions of articulation points of the person from the detected person area; and estimate an action of the person based on the detected positions of the articulation points and the detected object area.

8 Claims, 10 Drawing Sheets

(56) References Cited

U.S. PATENT DOCUMENTS

2020/0167947 A1\* 5/2020 Okazaki .................... G06T 7/70
2020/0245904 A1\* 8/2020 Ikeda ................. G06K 9/00523
2021/0056289 A1\* 2/2021 Kochi ................ G06K 9/00288

OTHER PUBLICATIONS

Notice of Opinion on the First Examination issued in corresponding Chinese Patent Application No. 201911125731.8 dated Dec. 15, 2020, with translation (15 pages).
Office Action issued in corresponding European Application No. 19204847.8, dated Apr. 9, 2021 (9 pages).

\* cited by examiner

STORAGE MEDIUM STORING IMAGE PROCESSING PROGRAM, AND IMAGE PROCESSOR

CROSS-REFERENCE TO RELATED APPLICATION

Japanese patent application No. 2018-219075 filed on Nov. 22, 2018, including description, claims, drawings, and abstract the entire disclosure is incorporated herein by reference.

BACKGROUND

Technical Field

The present invention relates to a storage medium storing image processing program, and an image processor.

2. Description of the Related Art

In our country, thanks to an improvement in standard of living resulting from the postwar rapid economic growth, an improvement of a hygienic environment, an improvement in medical level, and the like, remarkable life extension is being achieved. Therefore, in combination with a decrease in birth rate, we are experiencing an aging society in which an aging rate is high. In such an aging society, it is assumed that illness, injury, aging and the like will cause an increase in the number of persons in need of nursing care or the like, who require support such as caring.

There is a possibility that persons in need of nursing care, or the like, will topple down during walking, or will fall from a bed and consequently will be injured, in facilities such as a hospital and a nursing home. Accordingly, development of a system is being pushed forward, in the system, when a person in need of nursing care or the like is brought into such a state, in order to enable a staff member such as a care person and a nurse to dash to the person, an action of the person in need of nursing care or the like is detected from an image.

In relation to a technology for detecting an action of a person from a captured image, Japanese Patent No. 6119938 discloses the following technology. In the captured image, a boundary between an object area that includes an object such as a bed and another area is set beforehand, a person area in the image is detected, and the action such as getting up of the person is discriminated according to an overlapping width between the boundary and the person area.

SUMMARY

However, in the technology disclosed by Japanese Patent No. 6119938, since a posture or the like of the person is not taken into consideration, such an action that has merely stood in the vicinity of the bed cannot be suppressed from being falsely detected as getting into bed or the like. In addition, the action of the person is detected on the basis of relationship with a fixed object, and therefore it is not possible to cope with detection of the action of the person in relation to a moving object. Therefore, it is relatively difficult to further enhance detection accuracy in detecting the action of the person.

One or more embodiments of the present invention provide a storage medium storing image processing program and an image processor.

The storage medium storing image processing program and the image processor of one or more embodiments of the present invention comprises followings.

A non-transitory recording medium storing a computer readable image processing program that causes the computer to perform processing comprising:
(a) obtaining a captured image;
(b) detecting, from said image obtained in the (a), a person area that includes a person, and an object area that includes a predetermined object;
(c) estimating positions of articulation points of said person based on said person area detected in the (b); and
(d) estimating an action of said person based on said positions of said articulation points estimated in the (c), and said object area detected in the (b).

An image processor comprising a hardware processor that:
obtains a captured image;
detects, from said obtained image, a person area that includes a person, and an object area that includes a predetermined object;
estimates positions of articulation points of the person based on said detected person area; and
estimates an action of the person based on said estimated positions of said articulation points and said detected object area.

The features and characteristics of this invention other than those set forth above will become apparent from the description given herein below with reference to one or more embodiments illustrated in the accompanying drawings.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION

Figure 1:
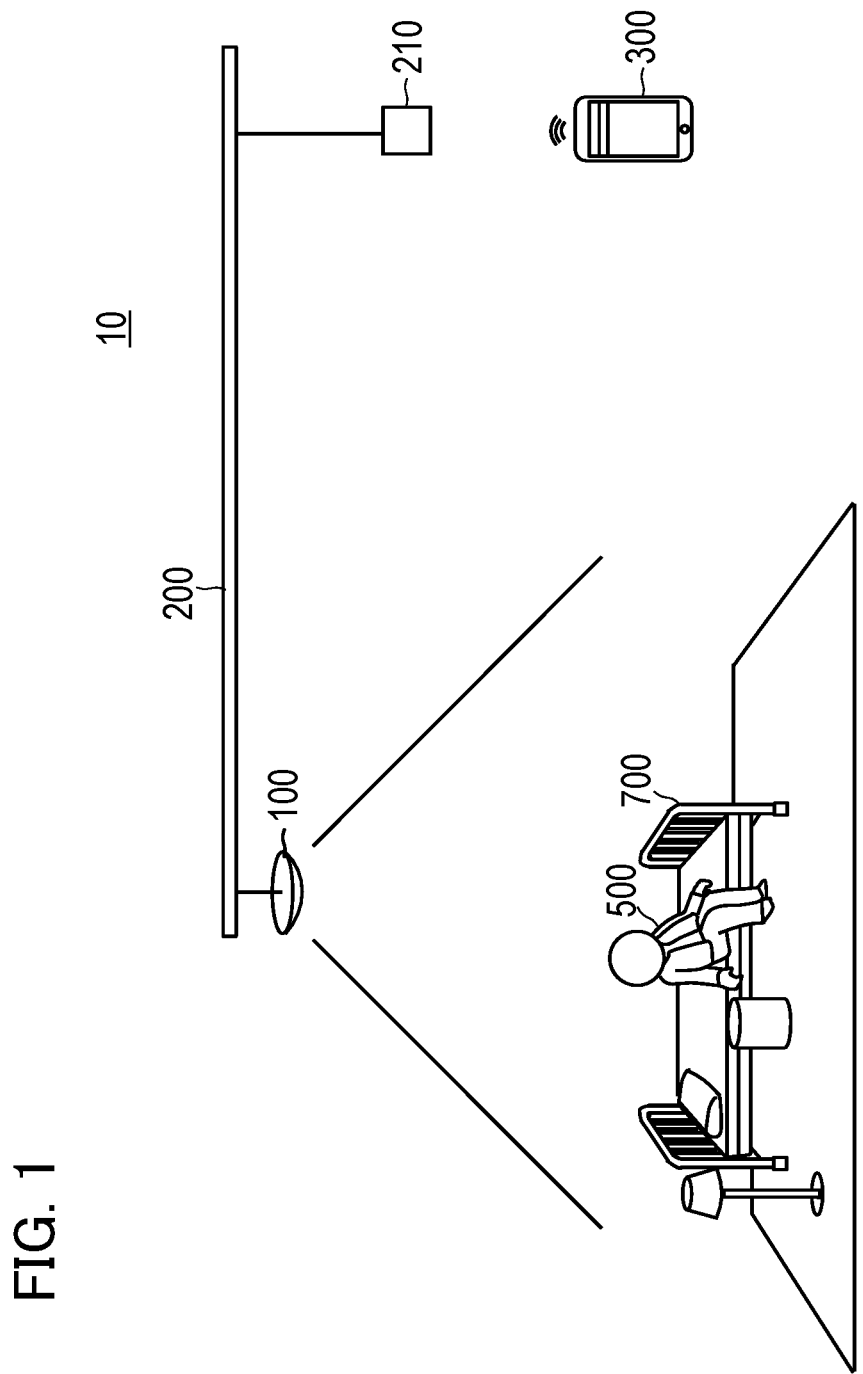
FIG. 1 is a drawing illustrating a schematic configuration of an image processing system according to one or more embodiments.

Hereinafter, embodiments of the present invention will be described with reference to the drawings. However, the scope of the invention is not limited to the disclosed embodiments.

An storage medium storing image processing program, and an image processor according to one or more embodiments of the present invention will be described below with reference to the drawings. It should be noted that in the drawings, identical elements are denoted by identical reference numerals, and overlapping explanation will be omitted. In addition, size ratios in the drawings are exaggerated for convenience of explanation, and thus may differ from the actual ratios.

First Example

[Whole Structure]

FIG. 1 is a drawing illustrating a schematic configuration of an image processing system 10.

The image processing system 10 includes a detector 100, a communication network 200, and a mobile terminal 300. The detector 100 is connected to the mobile terminal 300 so as to be capable of communicating with each other through an access point 210 by the communication network 200. The detector 100 configures an image processor. The detector 100 may be one unified device, or may be a plurality of devices that are separately arranged. It should be noted that by providing a server (not illustrated) that is capable of mutually communicating with a detector 100 and the mobile terminal 300 through the communication network 200, and the server may partially carry out a function of the detector 100. The mobile terminal 300 configures a notifier (notification device).

The detector 100 is arranged on, for example, a ceiling or the like of a living room of a target person 500. The target person 500 is, for example, a person who requires caring or nursing by a staff member or the like. The detector 100 image-captures a predetermined observation area to obtain an image (hereinafter merely referred to as "image 131" (refer to FIGS. 4 and 11)), and detects the target person 500 included in the image 131 as a person. As described later, the detector 100 detects an area in which an object exists on the captured image 131 (hereinafter referred to as "object existing area"). The detector 100 detects an object existing area in which a category of an object has been estimated to be a person (hereinafter, referred to as "person area 520" representing the person (refer to FIG. 11)) among the object existing areas, and thereby detects the target person 500 that is a person. The detector 100 detects the object existing area in which a category of an object has been estimated to be a predetermined object (hereinafter, referred to as "object area 810" representing the predetermined object (refer to FIGS. 4 and 11)) as the object area 810 with respect to categories among the object existing areas. The predetermined object includes a fixed object, and a moving object. The category of the predetermined object includes, for example, a chair, a bed, a wheelchair, and a walker. The detector 100 detects positions of articulation points 510 (refer to FIG. 4) from the person area 520. The position of each of the articulation points 510 corresponds to, for example, coordinates of each of the articulation points 510 in the image 131. The detector 100 estimates an action of the target person 500 based on the positions of the articulation points 510 and the object area 810. The action includes, for example, an action of having sat down on a chair, an action of having sat down on a bed, an action of having sat down on a floor, an action of having gotten up from the bed (getting up), an action of having left the bed (leaving the bed), an action of having fallen from the bed (falling down), and an action of toppling down to a floor surface or the like (toppling down). In a case where the estimated action is a predetermined action, the detector 100 transmits an event notification to the mobile terminal 300, the event notification notifying that an event related to the target person 500 has occurred. The predetermined action includes the action of having gotten up from the bed (getting up), the action of having left the bed (leaving a bed), the action of having fallen from the bed (falling down), and the action of having toppled down to a floor surface or the like (toppling down). The event is a change in state related to the target person 500, the change having been recognized by the detector 100. The event includes, for example, getting up, leaving the bed, toppling down, falling down, abnormality in slight body movement, and the like. A staff member should be notified (informed) of the event.

The detector 100 is capable of estimating the action of the target person 500 by using a deep neural network (hereinafter referred to as "DNN"). As a method for detecting a target object by DNN, publicly-known methods, including, for example, Faster R-CNN, Fast R-CNN, and R-CNN, can be mentioned. It should be noted that the detector 100 may estimate the action of the target person 500 by using machine learning other than DNN, for example, by using SVM (Support Vector Machine) or the like.

The mobile terminal 300 is carried by a staff member or the like who provides care including caring and nursing for the target person 500.

[Detector 100]

Figure 2:
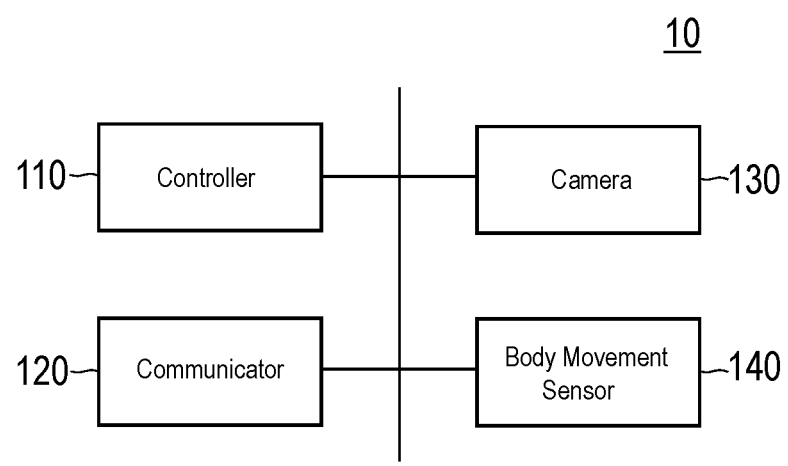
FIG. 2 is a block diagram illustrating a hardware configuration of a detector according to one or more embodiments.

FIG. 2 is a block diagram illustrating a hardware configuration of the detector 100. As shown in an example of FIG. 2, the detector 100 is provided with a controller 110, a communicator 120, a camera 130, and a body movement sensor 140. These are mutually connected through a bus.

The controller 110 is configured by a CPU (Central Processing Unit), and memories such as a RAM (Random Access Memory) and a ROM (Read Only Memory), and controls each part of the detector 100, and performs computation processing, according to a program. Functions of the controller 110 will be described later in detail.

The communication unit 120 is an interface circuit (for example, a LAN card, etc.) for communicating with the mobile terminal 300 or the like through the communication network 200.

The camera 130 is arranged, for example, in the upper part of the ceiling or wall of the living room of the target person 500, image-captures an area including a bed 700 of the target person 500 as a predetermined observation area, and outputs the image (image data). The image includes an image that includes the target person 500, and the above-described predetermined object. The image 131 includes a still image and a moving image. The camera 130 is a near-infrared ray camera. However, a visible light camera may be used as an alternative thereto, or the near-infrared ray camera and the visible light camera may be used in combination.

Figure 3:
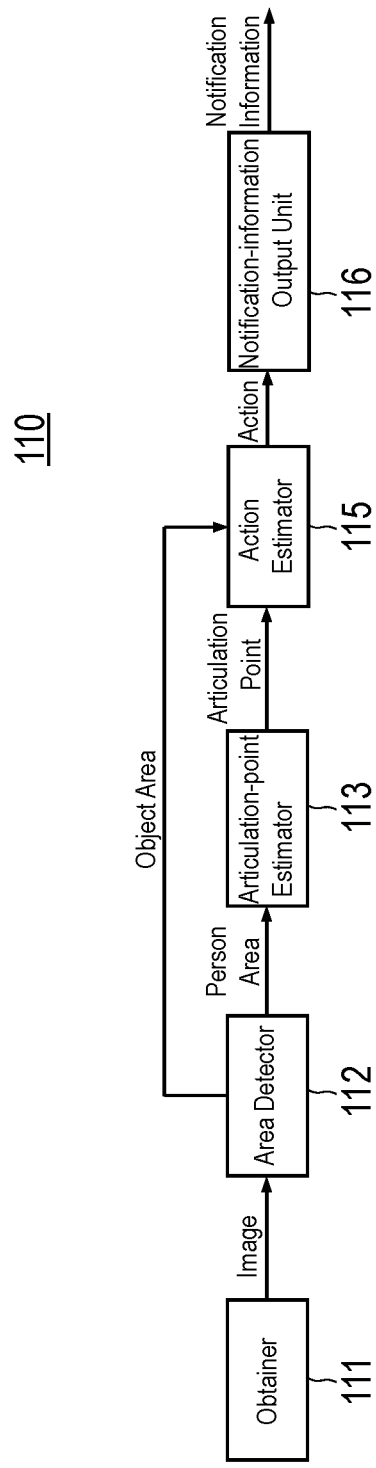
FIG. 3 is a functional block diagram of a controller according to one or more embodiments.

FIG. 3 is a functional block diagram of the controller 110. The controller 110 functions as an obtainer 111, an area detector (detector) 112, an articulation-point estimator 113, an action estimator 115, and a notification-information output unit 116.

The obtainer 111 obtains the image 131 from the camera 130. It should be noted that the obtainer 111 may obtain the image 131 by receiving, from another camera (not illustrated) other than the camera 130, the image 131 image-captured by the other camera, the other camera being connected to the detector 100 through the communication unit 120.

The area detector 112 detects the person area 520 and the object area 810 from the image 131. On the image 131, the area detector 112 detects, as an object existing area, an area in which an object exists, and calculates a reliability score for each category of objects included in the detected object existing area. The area detector 112 detects, as the person area 520, the object existing area in which the reliability score of a person category is the highest. Similarly, the object existing area in which the reliability score of the predetermined object category is the highest is detected as the object area 810 of the category in which the reliability score is the highest (for example, the object area of a chair).

The area detector 112 is capable of detecting the person area and the object area from the image 131 by DNN in which a dictionary (parameter) for detecting the person area 520 and the object area 810 from the image 131 is reflected.

The articulation-point estimator 113 estimates the articulation points 510 of the target person 70 based on the person area. The articulation-point estimator 113 is capable of estimating the articulation points 510 of the target person 70 from the person area 520 by DNN in which a dictionary for detecting the articulation points 510 from the person area 520 is reflected.

The action estimator 115 estimates the action of the target person 70 based on positions of the predetermined articulation points 510, and the object area 810.

Figure 4:
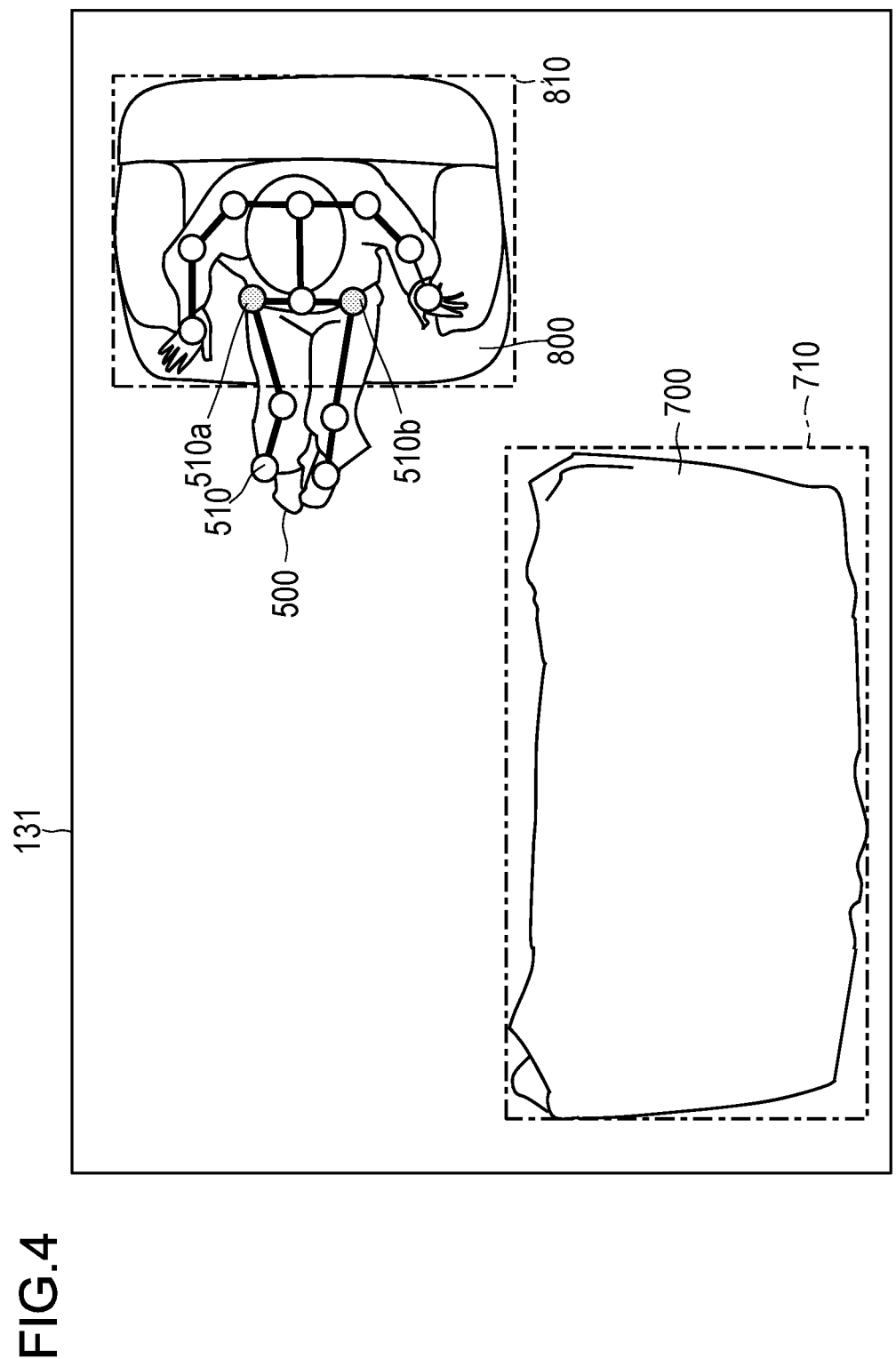
FIG. 4 is an explanatory drawing illustrating an example in which an action of a target person is estimated based on positions of predetermined articulation points and an object area according to one or more embodiments.

FIG. 4 is an explanatory drawing illustrating an example in which the action of the target person 500 is estimated based on positions of predetermined articulation points 510a, 510b, and the object area 810.

In the example of FIG. 4, a chair 800 is detected by the area detector 112 as the predetermined object of a chair category, and the object area 810 is shown as an area in a frame indicated by an alternate long and short dash line. Among the articulation points 510 of the target person 500, positions of the articulation points 510a, 510b of a waist are included inside the object area 810 of the chair category. Such positional relationship among positions of the articulation points 510a, 510b of the waist and the object area 810 of the chair category occurs when the target person 500 performs an action of having sat down on the chair 800. Therefore, in this case, the action estimator 115 estimates that the target person 500 has performed the action of having sat down on the chair 800. In this manner, the action estimator 115 estimates the action of the target person 500 based on positional relationship among positions of the predetermined articulation points 510 and the object area 810. The predetermined articulation points 510 are not limited to the articulation points 510a, 510b of the waist. For example, on the assumption that the predetermined articulation points 510 are articulation points 510 of the whole body (all articulation points), in a case where the predetermined articulation points 510 have come to be included inside the object area 710 of the bed 700 that is the predetermined object, it is possible to estimate that the target person 500 has performed an action of having got into the bed 700.

In a case where the action estimated by the action estimator 115 is the predetermined action, the notification-information output unit 116 transmits the event notification to the mobile terminal 300, which notifying that an event related to the target person 500 has occurred.

[Mobile Terminal 300]

Figure 5:
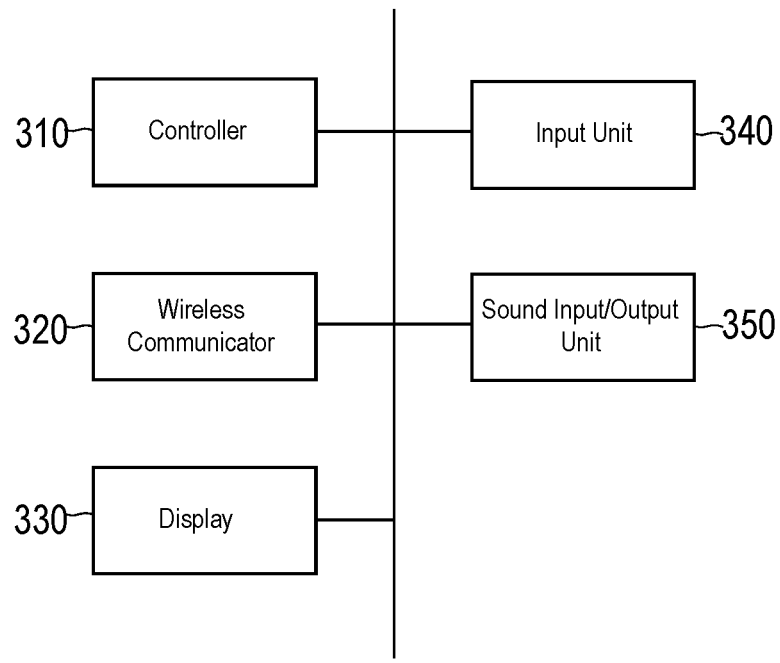
FIG. 5 is a block diagram illustrating a hardware configuration of a mobile terminal according to one or more embodiments.

FIG. 5 is a block diagram illustrating a hardware configuration of the mobile terminal 300. The mobile terminal 300 is provided with a controller 310, a wireless communicator 320, a display 330, an input unit 340, and a sound input/output unit 350. These are mutually connected through a bus. Basic configurations of these components are similar to corresponding components of the detector 100, and therefore overlapping explanation will be omitted. The mobile terminal 300 can be configured by portable communication terminal device such as, for example, a tablet type computer, a smart phone or a portable telephone.

The wireless communicator 320 performs wireless communication with a device such as the detector 100, the wireless communication using standards such as G4, Wi-Fi, and Bluetooth (registered trademark). The wireless communication with the device such as the detector 100 is performed through the access point 210, or is directly performed. The wireless communicator 320 receives the event notification from the detector 100.

The display 330 and the input unit 340 are provided as a touch panel. A touch sensor as the input unit 340 is superimposed on a display surface of the display unit 330 formed by a liquid crystal or the like. Various kinds of information and various instructions are displayed for a staff member or the like by the display 330 and the input unit 340. The display 330 displays contents of the event included in the event notification on the mobile terminal 300. In this manner, contents of the event are displayed on the mobile terminal 300, the contents being included in the event notification transmitted from the detector 100, and consequently the staff member or the like is notified of the contents of the event. The event notification configures information used to cause the mobile terminal 300 to notify the staff member or the like of the predetermined action of the target person 500. The input unit 340 accepts various operations such as input of a response to acceptance of coping with the event.

The sound input/output unit 350 includes, for example, a speaker and a microphone, and enables the staff member or the like to make a voice call with the mobile terminal of another staff member through the wireless communicator 320. It should be noted that in a case where the detector 100 is provided with a sound input/output unit, the sound input/output unit 350 enables to make a voice call with the detector 100 through the wireless communicator 320.

Figure 6:
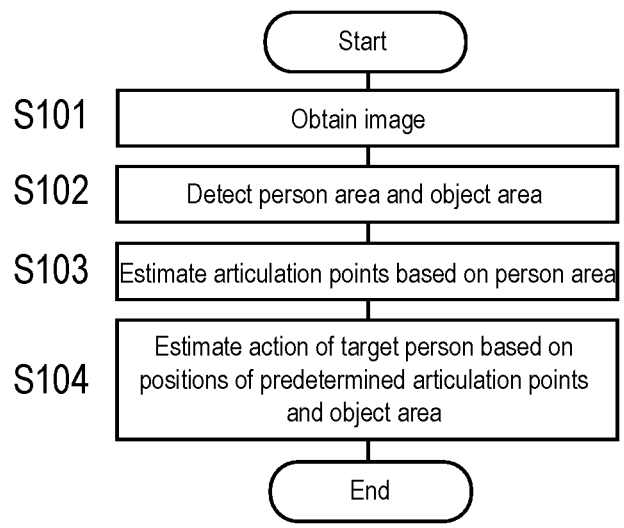
FIG. 6 is a flowchart illustrating operation of the detector according to one or more embodiments.

FIG. 6 is a flowchart illustrating operation of the detector 100. The present flowchart is executed by the controller 110 according to a program.

The controller 110 obtains the image 131 by the camera 130 (S101).

The controller 110 detects the person area 520 and the object area 810 from the image 131 (S102).

The controller 110 estimates positions of the articulation points 510 of the target person 500 based on the person area 520 (S103).

The controller 110 estimates the action of the person who is the target person 500 based on positional relationship among positions of the articulation points 510 and the object area 810 (S104).

Second Example

One or more embodiments according to a second example will now be described. Embodiments of the first example differ from embodiments of the second example as follows. According to one or more embodiments of the first example, the action of the target person 500 is estimated based on the positional relationship among the positions of the articulation points 510 and the object area 810. Meanwhile, according to one or more embodiments of the second example, a posture of the target person 500 is estimated from positions of the articulation points 510, and the action of the target person 500 is estimated based on the positions of the articulation points 510 of the target person 500, the posture of the target person 500, and the object area 810. With respect to points other than this point, one or more embodiments of the second example are similar to one or more embodiments of the first example, and therefore overlapping explanation will be omitted or simplified.

Figure 7:
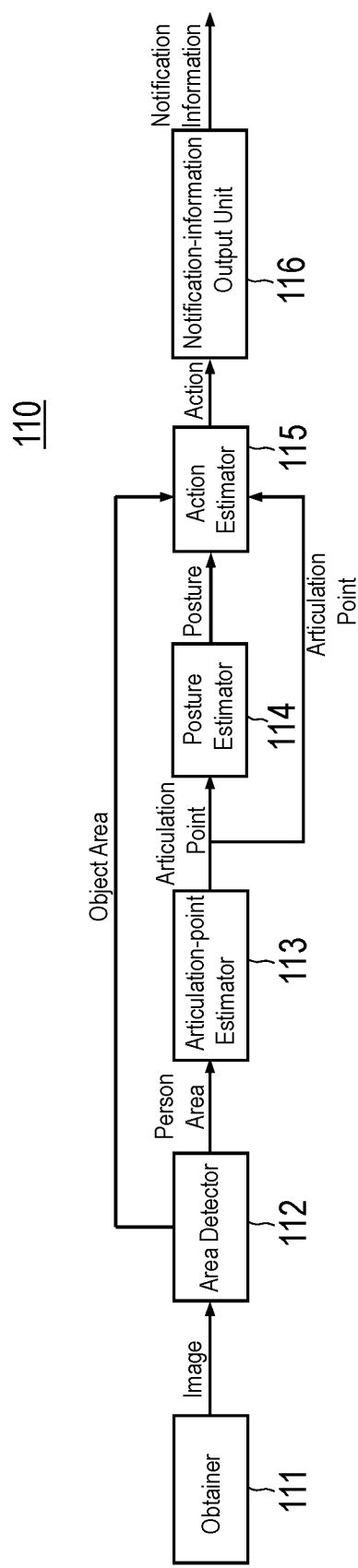
FIG. 7 is a functional block diagram of the controller according to one or more embodiments.

FIG. 7 is a functional block diagram of the controller 11. The controller 11 functions as the obtainer 111, the area detector 112, the articulation-point estimator 113, a posture estimator 114, the action estimator 115, and the notification-information output unit 116.

The obtainer 111 obtains the image 131, and the area detector 112 detects the person area 520 and the object area 810 from the image 131. The articulation-point estimator 113 estimates the articulation point 510 from the person area 520.

The posture estimator 114 estimates the posture of the target person 500 based on the positions of the articulation points 510 detected by the articulation-point estimator 113. The posture includes, for example, a standing position, a sitting position, and a recumbent position. The posture estimator 114 is capable of estimating the posture of the target person 500 from the positions of the articulation points 510 by DNN in which a dictionary for detecting a posture of a person from the positions of the articulation point 510 is reflected. Specifically, in a case where it has been estimated, by DNN, that the standing position is 5%, the sitting position is 87%, and the recumbent position is 8% as probabilities of posture classes based on the articulation points 510, the "sitting position" the probability of which is the highest, is estimated as the posture of the target person 500.

The action estimator 115 estimates the action of the target person 500 from the object area 810, the positions of the articulation points 510 of the target person 500, and the posture of the target person 500. For example, in a case where positions of the articulation points 510a, 510b of a waist (refer to FIG. 4) among the articulation points 510 of the target person 500, are included inside the object area 810 of the category of the chair 800, and the posture has become the sitting position posture, the action estimator 115 estimates that the target person 500 has performed an action of having sat down on the chair 800. In this manner, the action estimator 115 estimates the action of the target person 500 based on the positional relationship among positions of the predetermined articulation points 510 and the object area 810, and the posture. For example, it cannot be said that there is no possibility that on the image 131, while the target person 500 takes a standing position posture, the positions of the articulation points 510a, 510b of the waist will be included inside the object area 810 of the category of the chair 800. In such a case, according to one or more embodiments of the first example, it is falsely detected that the target person 500 has performed the action of having sat down on the chair 800. Meanwhile, according to one or more embodiments of the second example, such a false detection can be suppressed.

Figure 8:
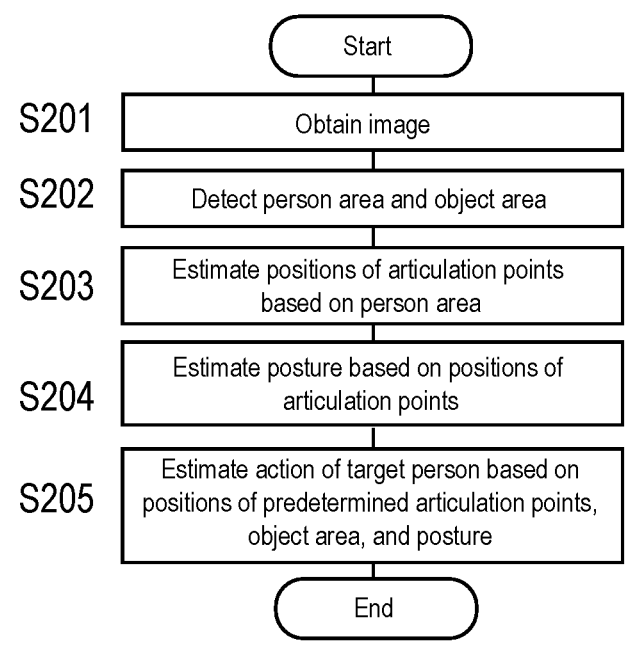
FIG. 8 is a flowchart illustrating operation of the detector according to one or more embodiments.

FIG. 8 is a flowchart illustrating operation of the detector 100.

The controller 110 obtains the image 131 (S201), and detects the person area 520 and the object area 810 from the image 131 (S202).

The controller 110 estimates the positions of the articulation points 510 of the target person 500 based on the person area 520 (S203).

The controller 110 estimates the posture of the target person 500 based on the positions of the articulation points 510 (S204).

The controller 110 estimates the action of the target person 500 based on the relationship among the positions of the predetermined articulation points 510 of the target person 500 and the object area, and the posture of the target person 500 (S205).

Third Example

One or more embodiments according to a third example will now be described.

Embodiments of the first example differ from embodiments of the third example as follows. According to one or more embodiments of the first example, for each frame of the image 131, the action of the target person 500 is estimated based on the positions of the articulation points 510 and the object area 810. Meanwhile, according to one or more embodiments of the third example, based on the positions of the articulation points 510 and the object area 810, which have been detected respectively from each of a plurality of frames of the image 131, an action of the target person 500 is estimated from temporal changes of the articulation points 510 and the object area 810. With respect to points other than this point, one or more embodiments of the third example are similar to one or more embodiments of the first example, and therefore overlapping explanation will be omitted or simplified.

Figure 9A:
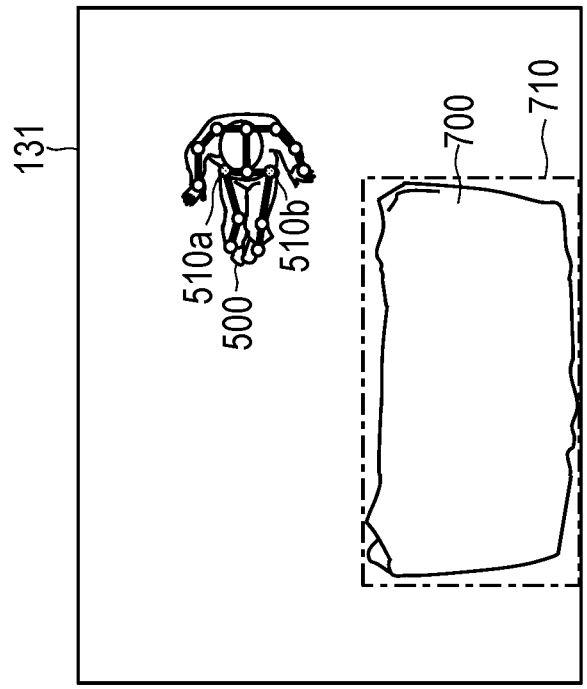
FIG. 9A is a drawing illustrating a state in which positions of articulation points of a target person and an object area are detected in an image according to one or more embodiments.
Figure 9B:
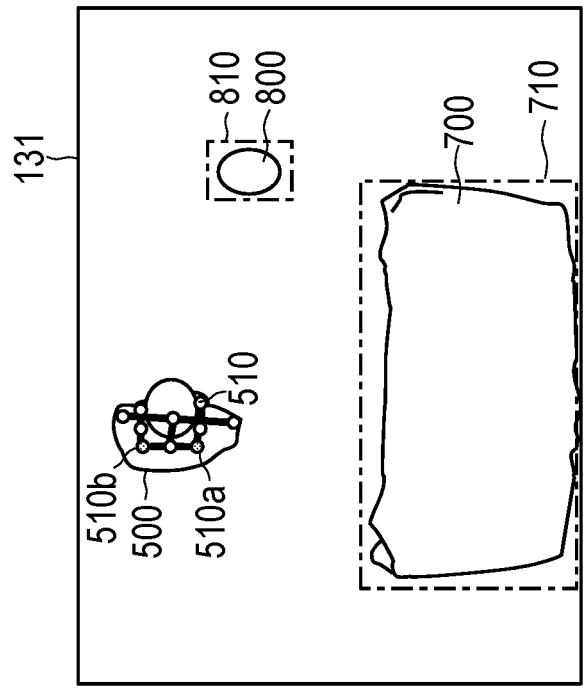
FIG. 9B is a drawing illustrating, in image temporally adjacent to the image in FIG. 9A, a state in which positions of articulation points of the target person and the object area are detected.

FIG. 9A and FIG. 9B are drawings each illustrating, in the images 131 that are temporally adjacent to each other, a state in which positions of articulation points 510 of the target person 500 and the object area 810 have been detected. FIG. 9A shows the image 131 obtained by image-capturing, a state in which the target person 500 is walking with a posture of a standing position while facing a direction of the chair 800. FIG. 9 shows the image 131 of a frame that is temporally posterior to the frame of the image 131 in FIG. 9A, and shows the image 131 obtained by image-capturing, a state in which the target person 500 takes a posture of a sitting position on a seat surface of the chair 800.

In the image 131 shown in FIG. 9A, the chair 800 has been detected as the predetermined object, and consequently the object area 810 is displayed as a rectangle indicated with an alternate long and short dash line that surrounds the chair 800. In addition, the target person 500 has been detected as the person area 520, and positions of the articulation points 510 have been estimated from the person area 520. Consequently, the positions of the articulation points 510 are displayed.

Meanwhile, in the image 131 shown in FIG. 9B, since the target person 500 sits down on the seat surface of the chair 800, the chair 800 is hidden by the target person 500, and consequently an image of the chair 800 disappears on the image 131. Therefore, the chair 800 is not detected as the object area 810. As the result, the object area 810 is not displayed. Therefore, estimating the action of the target person 500 merely by the image 131 shown in FIG. 9B will fail to estimate a correct action of the target person 500 who is sitting down on the chair 800. In this case, it may be falsely estimated that the target person 500 has performed an action of sitting down on a floor (floor sitting position).

According to one or more embodiments of the third example, the action of the target person 500 is estimated from temporal changes of the articulation points 510 and the object area based on the positions of the articulation points 510 and the object area 810, the positions of the articulation points 510 having been detected from each of the plurality of frames of the image 131. Specifically, in a case where the predetermined object (for example, the chair 800) that has been detected disappears on the image 131, consequently the object area 810 has been lost, it is estimated that the object area 810 has been hidden by the target person 500 or the like. The object area 810 of the predetermined object that has been detected in the image 131 of the frame before the object area 810 has been lost is applied as the object area 810 in the image 131 of the frame after the object area 810 has been lost. As the result, for example, the object area 810 of the chair 800 in the image 131 of FIG. 9A is applied as the object area 810 in the image 131 of FIG. 9B. Therefore, in the image 131 of FIG. 9B, among the articulation points 510 of the target person 500, the articulation points 510a, 510b of the waist, which are the predetermined articulation points 510, are brought into a state of being included inside the object area 810 of the chair 800, and therefore the action of having sat down on the chair 800, which has been performed by the target person 500, is correctly detected.

As with one or more embodiments of the second example, one or more embodiments of the third example may be applied in the case where the posture of the target person 500 is estimated from positions of the articulation points 510, and the action of the target person 500 is estimated based on the positions of the articulation points 510 of the target person 500, the posture of the target person 500, and the object area 810. For example, it is assumed that in a plurality of frames that are relatively temporally adjacent, a standing position posture is estimated from the articulation points 510 of the target person 500 on based on the captured image 131 in a temporally previous frame, and a sitting position posture is estimated from the articulation points 510 of the target person 500 based on the captured image 131 in a posterior frame. In addition, it is assumed that the object area 810 of the chair 800 or the like is detected in the image 131 in neither of the frames. In this case, it is not estimated that the object area 810 of the chair 800 or the like has been hidden by the target person 500 or the like. Therefore, an action that the target person 500 has toppled down on the floor can be properly detected.

Figure 10:
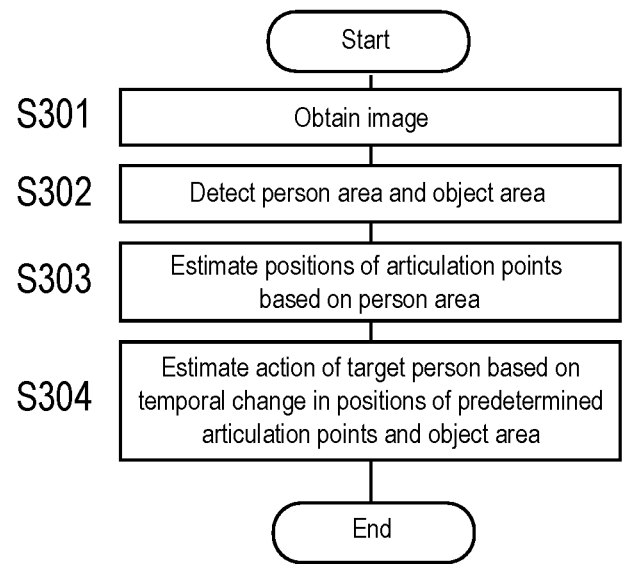
FIG. 10 is a flowchart illustrating operation of the detector according to one or more embodiments.

FIG. 10 is a flowchart illustrating operation of the detector 100.

The controller 110 obtains the image 131 (S301), and detects the person area 520 and the object area 810 from the image 131 (S302).

The controller 110 estimates positions of the articulation points 510 of the target person 500 based on the person area 520 (S303).

The controller 110 estimates the action of the target person 500 based on the temporal change of the positions of the predetermined articulation points 510 of the target person 500 and the object area 810 (S304).

Fourth Example

One or more embodiments according to a fourth example will now be described. Embodiments of the first example differ from embodiments of the fourth example as follows. According to one or more embodiments of the first example, the person area 520 and the object area 810 are detected from the whole image 131. Meanwhile, according to one or more embodiments of the fourth example, the person area 520 is detected from the whole captured image 131, a candidate area 530 (refer to FIG. 12) that includes the person area 520, and that is larger than the person area 520 is set based on the person area 520, and the object area 810 is detected from the candidate area 530. With respect to points other than this point, one or more embodiments of the fourth example are similar to one or more embodiments of the first example, and therefore overlapping explanation will be omitted or simplified.

Figure 11:
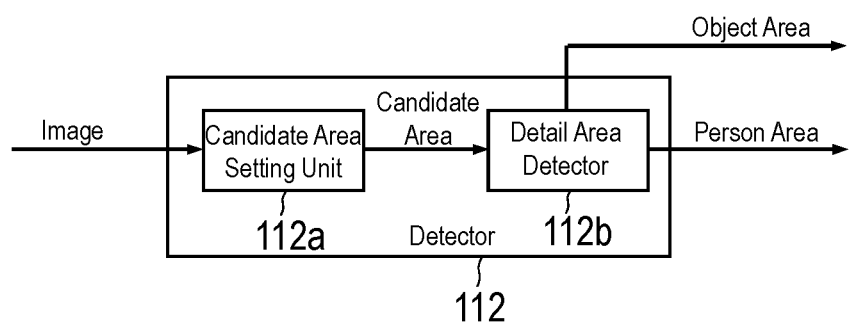
FIG. 11 is a functional block diagram of an area detector according to one or more embodiments.
Figure 12:
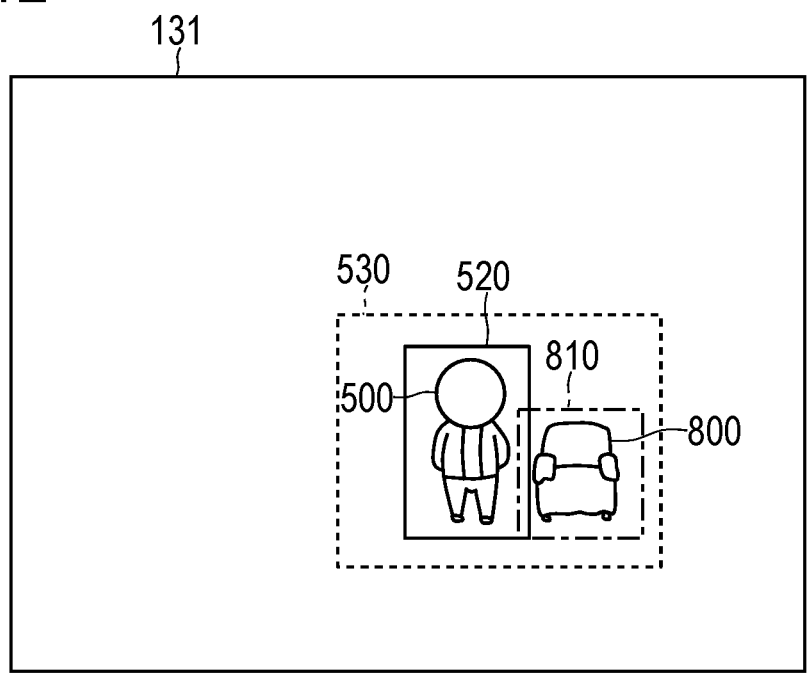
FIG. 12 is an explanatory diagram illustrating a candidate area according to one or more embodiments.

FIG. 11 is a functional block diagram of an area detector 112. The area detector 112 includes a candidate area setting unit 112a, and a detail area detector 112b. FIG. 12 is an explanatory diagram for explaining the candidate area 530.

The candidate area setting unit 112a detects the person area 520 from the image 131, and sets the candidate area 530 based on the person area 520. The candidate area setting unit 112a is capable of detecting the person area 520 from the image 131 by DNN in which a dictionary for detecting the person area 520 from the image 131 is reflected.

The candidate area setting unit 112a sets the candidate area 530 as an area that includes the person area 520, and that is smaller than the image 131 and is larger than the person area 520. The candidate area 530 can be set as, for example, a rectangular area, the center of which is the center of gravity of the person area 520, the rectangular area having a predetermined size and a predetermined aspect ratio. The predetermined size and the predetermined aspect ratio can be set at arbitrary appropriate values by experiment.

The detail area detector 112b detects the person area 520 and the object area 810 from the candidate area 530. The detail area detector 112b is capable of detecting the person area 520 and the object area 810 from the candidate area 530 by DNN in which a dictionary for detecting the person area 520 and the object area 810 from the candidate area 530 (a part of the image 131) is reflected. Since the candidate area 530 is smaller than the image 131, a detection range of the object area 810 can be reduced. This enables to shorten the total detection time required to detect the person area 520 and the object area 810. It should be noted that since the detection range for detecting the object area 810 is limited to the candidate area 530, the predetermined object detected as the object area 810 includes only an object that is relatively close to the person area 520.

It should be noted that the detail area detector 112b may detect only the object area 810. In this case, as the person area 520, a result of detecting the person area 520 by the candidate area setting unit 112a can be used.

Figure 13:
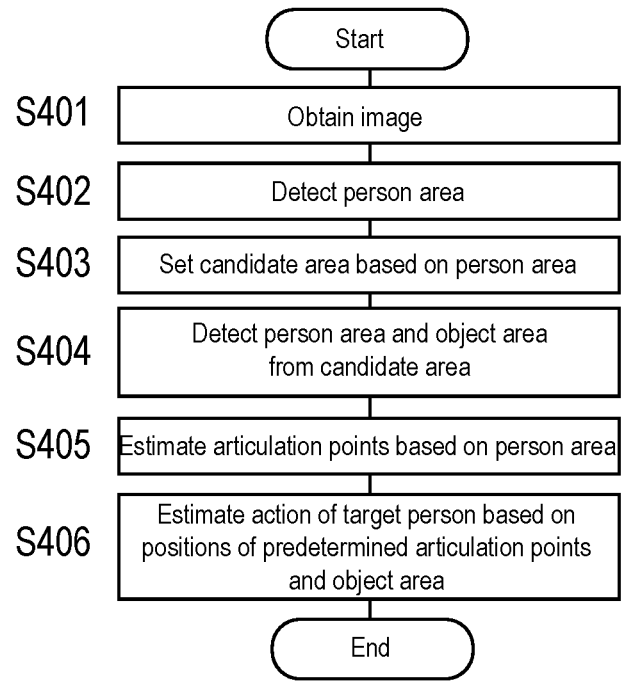
FIG. 13 is a flowchart illustrating operation of the detector according to one or more embodiments.

FIG. 13 is a flowchart illustrating operation of the detector 100.

The controller 110 obtains the image 131 (S401), and detects the person area 520 from the image 131 (S402).

The controller 110 sets the candidate area 530 based on the person area 520 (S403).

The controller 110 detects the person area 520 and the object area 810 from the candidate area 530 (S404).

The controller 110 estimates positions of the articulation points 510 of the target person 500 based on the person area 520 (S405).

The controller 110 estimates the action of the target person 500 based on the positions of the articulation points 510 and the object area 810 (S406).

According to the above embodiments, the target person 500 is, for example, the person who requires caring or nursing, and the action of the target person 500 is detected based on the image 131 image-captured by the camera 130 of the detector 100, that is arranged on the ceiling or the like of the living room of the target person 500. In addition, in a case where the detected action is the predetermined action, occurrence of the event is notified by transmitting the event notification to the mobile terminal 300.

Meanwhile, in one or more embodiments of the fourth example, the camera 130 is arranged on a ceiling or the like of a convenience store, and an action of a customer of the convenience store or the like is detected based on the image 131 captured by the camera 130. In this case, the person area 520 is detected as an area that includes an image of the customer, and the object area 810 is detected as an area that includes a predetermined commodity exhibited in a commodity shelf. In addition, as the action of the customer who is the target person 500, for example, an action of taking an alcoholic liquor placed on the top stage of the fifth shelf, an action of taking a shampoo placed on the second stage of the fifth shelf, and an action of stopping while keeping the face toward the fifth shelf or the like, are detected. Such actions of the target person 500 can be used for, for example, rearrangement of commodities, a layout change of shelves, or the like, as marketing information.

The embodiments according to the present invention have the following effects.

The person area that includes the person and the object area that includes the predetermined object are detected from the captured image, and the action of the person is estimated based on positions of articulation points estimated from the person area, and the object area. This enables to estimate the action of the person with high accuracy.

Further, the posture of the person is estimated based on the estimated positions of the articulation points, and the action of the person is estimated based on the positions of the articulation points, the posture, and the object area. This enables to estimate the action of the person with higher accuracy.

Further, by using the neural network in which the dictionary for detecting the person area and the object area from the image is reflected, the person area and the object area are detected from the image. This enables to estimate the action of the person simply and at high speed, and to further enhance the estimated accuracy.

Further, the person area is detected from the image, the candidate area is set as the area that includes the person area, and that is smaller than the image, and is larger than the person area, and the person area and the object area are detected from the candidate area. As the result, by reducing the detection range of the candidate area, the action of the person can be estimated with high speed and high accuracy.

Further, based on positional relationship among positions of the predetermined articulation points among the estimated positions of the articulation points and the object area, an action is estimated. This enables to estimate an action of the person more easily and with high accuracy.

Further, the action of the person is estimated based on the temporal change in the relationship among positions of articulation points and an object area. Consequently, even if the predetermined object is hidden by the person, the action of the person can be estimated with high accuracy.

Further, based on the temporal change in the relationship among the positions of articulation points, the posture, and the object area, the action is estimated. Consequently, by detecting the change in state of the target person based on temporally adjacent images, the action including toppling down and the like of the target person, the importance level of which is high, can be detected with higher accuracy.

Further, in the case where the estimated action is the predetermined action, information for causing the notifier to perform notification is output. Consequently, for example, when the event occurs, the occurrence of the event can be simply and quickly informed.

The configuration of the image processing system described above is main configurations to describe the features of the above-described embodiments. Therefore, the configurations are not limited to the above-described configurations, and can be modified in various ways within the scope of the claims. In addition, it is not intended to exclude a configuration included in a general image processing system.

For example, the mobile terminal may be provided with a part of a function of the detector.

Each of the image recognition device, the image capturing device, and the mobile terminal may be configured by a plurality of devices, and any of the plurality of devices may be configured as a single device.

With respect to the flowcharts described above, steps may be partially omitted, or other steps may be added thereto. In addition, a part of each step may be concurrently executed, or one step may be executed by being divided into a plurality of steps.

In the embodiments described above, the explanation has been made on the assumption that the action of the person is detected. However, an action detection object may be an animal.

A means and method for performing various processing in the above-described image processing system can be realized by dedicated hardware circuitry or a programmed computer. The above-described program may be provided, for example, by a computer readable recording medium such as a USB memory and a DVD (Digital Versatile Disc)-ROM, or may be provided online through a network such as the Internet. In this case, the program recorded on the computer readable recording medium is usually transmitted to a storage unit such as a hard disk, and is then stored therein. Furthermore, the above-described program may be provided as independent application software, or as one function, may be built into software of a device thereof such as the detector.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A non-transitory recording medium storing a computer readable image processing program that causes a computer to:

obtain a captured image;

detect, from the obtained image, a person area representing a person and an object area representing a predetermined object;

detect positions of articulation points of the person from the detected person area;

estimate an action of the person based on a relative position of one of the detected positions with respect to the detected object area;

in a case where the object area has been lost after detecting the object area, apply the detected object area before the object area has been lost as the object area after the object area has been lost; and estimate an action of the person based on the relative position with respect to the applied object area.

2. The non-transitory recording medium according to claim 1, wherein the program further causes the computer to:

estimate a posture of the person based on the detected positions; and estimate the action based on the estimated posture and the relative position.

3. The non-transitory recording medium according to claim 1, wherein the program further causes the computer to detect the person area and the object area from the obtained image by using a neural network that reflects a parameter for detecting the person area and the object area from the obtained image.

4. The non-transitory recording medium according to claim 1, wherein the program further causes the computer to detect the person area and the object area from a candidate area that includes the person area, and the candidate area is smaller than the obtained image and larger than the person area.

5. The non-transitory recording medium according to claim 1, wherein the program further causes the computer to estimate the action based on a temporal change in relationship between the detected object area and the detected positions.

6. The non-transitory recording medium according to claim 2, wherein the program further causes the computer to estimate the action based on a temporal change in relationship among the estimated posture, and the detected object area, and the detected positions.

7. The non-transitory recording medium according to claim 1, wherein the program further causes the computer to when the estimated action is a predetermined action, output information for performing notification.

8. An image processor comprising a hardware processor that:

obtains a captured image;

detects, from the obtained image, a person area representing a person and an object area representing a predetermined object;

detects positions of articulation points of the person from the detected person area;

estimates an action of the person based on a relative position of one of the detected positions with respect to the detected object area;

in a case where the object area has been lost after detecting the object area, applies the detected object area before the object area has been lost as the object area after the object area has been lost; and estimates an action of the person based on the relative position with respect to the applied object area.

* * * * *